United States Patent [19]
Marburg et al.

[11] Patent Number: 4,830,852
[45] Date of Patent: * May 16, 1989

[54] COVALENTLY-MODIFIED NEUTRAL BACTERIAL POLYSACCHARIDES, STABLE COVALENT CONJUGATES OF SUCH POLYSACCHARIDES AND IMMUNOGENIC PROTEINS AND METHODS OF PREPARING SUCH POLYSACCHARIDES AND CONJUGATES

[75] Inventors: Stephen Marburg, Metuchen; Richard L. Tolman, Warren; Deborah A. Jorn, Metuchen, all of N.J.

[73] Assignee: Merck & Co Inc., Rahway, N.J.

[*] Notice: The portion of the term of this patent subsequent to Sep. 22, 2004 has been disclaimed.

[21] Appl. No.: 35,241

[22] Filed: Apr. 6, 1987

Related U.S. Application Data

[63] Continuation of Ser. No. 684,401, Dec. 20, 1984, abandoned.

[51] Int. Cl.$^4$ .................... C07K 15/04; A61K 37/00; A61K 39/02

[52] U.S. Cl. .................... 424/85.8; 424/92; 424/88; 424/87; 530/395; 530/402; 530/403; 530/404; 530/405; 530/406; 536/55.1; 536/1.1; 536/123; 514/54; 514/885

[58] Field of Search .................... 424/88, 92; 530/395, 530/402–406; 536/55.1, 1.1, 123; 514/54

[56] References Cited

U.S. PATENT DOCUMENTS 4,613,665  9/1986  Larm .................... 525/54.2
4,673,574  6/1987  Anderson .................... 424/92

Primary Examiner—Howard E. Schain
Assistant Examiner—Garnette D. Draper
Attorney, Agent, or Firm—Richard S. Parr; Hesna J. Pfeiffer

[57] ABSTRACT

Covalently-modified neutral bacterial polysaccharides; covalent conjugates of such polysaccharides linked by a bigeneric spacer, with immunogenic bacterial membrane or other proteins, which conjugates are useful components of bacterial vaccines; and methods of preparing such polysaccharides and conjugates.

11 Claims, No Drawings

COVALENTLY-MODIFIED NEUTRAL BACTERIAL POLYSACCHARIDES, STABLE COVALENT CONJUGATES OF SUCH POLYSACCHARIDES AND IMMUNOGENIC PROTEINS AND METHODS OF PREPARING SUCH POLYSACCHARIDES AND CONJUGATES

The present application is a continuation of U.S. patent applicaiton, Ser. No 684,401, filed Dec. 20, 1984, now abnadoned.

The present invention is directed to covalently-modified neutral bacterial polysaccharides, specifically to pneumococcal 14 and similar polysaccharides, and to covalent conjugates of such polysaccharides linked by a bigeneric spacer, which permits proof of covalency and facilitates purification and concentration of biologically-desirable entities, with immunogenic bacterial membrane or other proteins, which conjugates are useful components of bacterial vaccines. The present invention also relates to methods of preparing such polysaccharides and conjugates.

BACKGROUND OF THE INVENTION

Purified capsular polysaccharides of bacteria have been used to prepare vaccines against the cognate bacteria, but the resulting immune responses have often been less satisfactory than desirable, especially in very young children or individuals with immature or deficient immunological systems. The *Streptococcus pneumoniae* type 14 capsular polysaccharide, for example, fails to provoke an immune response in infants, thus making this polysaccharide ineffective by itself in providing protection against the serious pediatric medical problems caused by *Streptococcus pneumoniae* type 14 bacteria, see, for example, Douglas et al., *J. Infect. Diseases*, 148, 131–137 (1983) and Laurence et al., *Am. J. Diseases of Children*, 137, 846–850 (1983). Enhancement of the immunogenicity of these polysaccharides may often be accomplished by combining them with proteins, Schneerson et al., *Infection and Immunity*, 45, No. 3, 582–591 (1984) (discussing conjugation of *Streptococcus pneumoniae* type 6A).

Care must be exercised in the selection of the protein which is to be combined with these polysaccharides, however. Certain proteins (e.g., pertussinogen) are non-specific stimulators of the immune system in infants. These proteins can, to a degree, enhance the immune response to polysaccharide antigens, but unfortunately, such non-specific activation leads to unwanted biological effects (i.e., reactogenicity). The much preferred specific enhanced immune responses to these polysaccharide antigens can be achieved in infants by "conjugating" these polysaccharides to appropriate proteins, as first reported by W. F. Goebel and O. T. Avery in 1929 (*J. Exptl. Medicine* 50, 521–531 (1929)).

The means of combining the polysaccharide and protein must also be carefully considered. If, as is believed, the immunological enhancement is realized as a result of the molecular proximity of the polysaccharide determinants to the protein "carrier" determinants, these moieties should not easily separate in the biological system. Non-covalent complexes, arising from the polyanioic character of many polysaccharides and the polycationic character of "carrier" proteins, may stimulate immune responses, but these complexes are chemically labile and the resultant immune responses appear to show T-cell independency. By contrast, covalent conjugates of polysaccharides and protein would possess much greater chemical stability and could demonstrate T-cell-dependent immune responses.

Covalent polysaccharide-protein conjugates have been claimed in the literature, but the exact nature of the covalent linkage has not been proven or quantified since the only assay for covalency has been activity in vivo. In addition, the processes disclosed in the literature have poor reproducibility. *Haemophilus influenzae* type b and *Streptococcus pneumoniae* type 6A polysaccharides were reacted with cyanogen bromide, then with adipic acid dihydrazide, then "coupled" with tetanus toxoid or horseshoe crab hemocyanin proteins in Schneerson et al. *J. Exptl. Med.*, 152, 361 (1980) and *Infection and Immunity*, 40, 245 (1983). Pneumococcal type 19F polysaccharide was coupled to bovine serum albumin directly by forming imines (Schiff bases) from the reducing ends of the polysaccharides and the pendant amine groups (i.e., lysines) of the protein, then reducing these imines with sodium cyanoborohydride (Lin et al., *Immunology*, 46, 333 (1982)).

Additionally, polysaccharides linked to diazotized aromatic amines were coupled to the protein's tyrosines in K. K. Nixdorff et al., *Immunology* 29, 87 (1975) and polysaccharides linked to aromatic amines were converted to isothiocyanates, which were then linked to the pendant amino groups of the protein's lysine in S. B. Svenson and A. A. Lindberg, *J. Immunolog. Methods* 25, 323 (1979). In each case, however, the resulting conjugate was characterized only by its gel permeation chromatographic behavior. In still another example (S. Nutani et al., *Infection and Immunity* 36, 971 (1982)), the polysaccharide, pullulan, was activated with cyanuric chloride, then reacted with tetanus toxoid. In this case, the conjugates were characterized by electrophoresis and only shown to be different from the starting materials.

In none of these cases was covalency demonstrated other than by the implications of an aggregated molecular weight, thereby confusing covalency with the natural interaction of macromolecular species, with and without charges, in molecular complexes, as these complexes will also give an aggregate molecular weight.

In copending application, U.S. Ser. No. 608,738, filed May 10, 1984, (and incorporated herein by reference) covalently-modified polyanionic polysaccharides and proteins have now been shown, together with covalent conjugates of such polysaccharides linked by abigeneric spacer with immunogenic bacterial membrane or other proteins and methods of preparing these and of confirming the covalency of the linkage between polysaccharides and proteins. Using the methodology of this reference, it is now possible to produce chemically-stable polysaccharide-protein conjugates which demonstrate T-cell dependency and which would be useful as vaccine components for eliciting protective serum antibodies to, particularly, the cognate bacteria of the polysaccharides used. This methodology is, however, only useful for covalently-modifying polyanionic polysaccharides and has not been useful with intractable polysaccharides which are insoluble or only semi-soluble in organic solvents or salt solutions.

It was, therefore, an object of this invention to develop a method for solubilizing neutral polysaccharides and covalently-modifying these neutral polysaccharides in preparation for preparing chemically-stable polysaccharide-protein conjugates. It was also an object of this invention to link neutral polysaccharide determinants to protein "carrier" determinants, in chemically-stable conjugates, such that the molecular proximity of these moieties could be maintained in biological systems in order that these conjugates would be useful as components in a mono- or polyvalent vaccine for eliciting protective serum antibodies to certain bacteria, particularly the cognate bacteria of the polysaccharides used. It was a further object of this invention to develop methods of treatment employing these conjugates in immunologically-effective vaccines for use against, e.g., meningitis and otitis media.

SUMMARY OF THE INVENTION

The present invention is directed to covalently-modified neutral bacterial polysaccharides and to chemically-stable conjugates of such neutral polysaccharides with covalently-modified immunogenic membrane proteins, viral protein subunits, synthetic polypeptides, bacterial toxoids or other suitable immunogenic proteins, which conjugates are useful components of immunogenic bacterial vaccines. The polysaccharide-protein conjugates of this invention are coupled through bigeneric spacers containing a covalent thioether group, wherein the bigeneric spacers are atom chains linking macromolecules (such as neutral polysaccharides and proteins), part of which spacers originate with one modified macromolecule (e.g., the covalently-modified neutral polysaccharide) and the other part of which originate with the other modified macromolecule (e.g., the functionalized protein).

In the process according to the instant invention, the neutral polysaccharide is covalently functionalized in one or more steps to produce a polysaccharide with pendant electrophilic centers or pendant thiol groups. Preferably, the neutral polysaccharide is first fragmented by heating in water with or without aqueous hydrazine, the water is removed, and the fragmented polysaccharide is derivatized with a bifunctional activation agent before being reacted with a bis-nucleophile. The nucleophile-functionalized neutral polysaccharide is then either reacted with a reagent to generate pendant electrophilic sites or reacted with a reagent to generate pendant thiol groups. By proper selection of the bis-nucleophile, i.e., one which would react with the activated neutral polysaccharide and result in a covalently-modified polysaccharide with pendant electrophilic sites or thiol groups, or selection of the proper nucleophile, further functionalization of the nucleophile-functionalized neutral polysaccharide may be avoided.

Independent of the covalent modification of the neutral polysaccharide, the appropriate bacterial "carrier" protein is reacted with reagents generating pendant thiol groups or with reagents generating pendant electrophilic centers, in either a one- or two-step process. The appropriately covalently-modified neutral polysaccharides and proteins are then reacted to form covalent polysaccharide-protein conjugates and purified to remove unconjugated macromolecules and excess reagents in order to permit the immunogenic dosage to be based on the amount of covalently-linked polysaccharide in the conjugate form.

Immunogenic monovalent or polyvalent vaccines containing immunologically-effective amounts of the polysaccharide-protein conjugates according to this invention or mixtures of the polysaccharide-protein conjugates according to this invention with other covalent polysaccharide-protein conjugates, such as those described in U.S. Ser. No. 608,738, filed May 10, 1984, or with other immunologic materials, or their derivatives may then be prepared.

DETAILED DESCRIPTION OF THE INVENTION

The covalently-modified polysaccharides of this invention may be modified versions of any neutral (i.e., nonanionic/nonacidic) polysaccharides, and are not intended to be limited to any particular types. Examples of such neutral bacterial capsular polysaccharides include *Streptococcus pneumoniae* (pneumococcal) types 14, 7F and 37 polysaccharides, described in L. Kenne and B. Lindberg in *The Polysaccharides*, Vol. II, pp. 287–363, Academic Press (1983) and A. S. Chaudri et al., *Carbohydrate Research*, 25, 161–172 (1972).

The proteins according to this invention are those of proven safety and demonstrable immunogenicity, but are not limited to any particular type. Suitable proteins include bacterial membrane proteins; any of various plant proteins, such as edestin or soybean trypsin inhibitor; viral protein subunits, such as hepatitis A or B, herpes gD or gC, Epstein-Barr or varicella zoster subunits; synthetic polypeptides; diphtheria toxoid; or tetanus toxoid, but are preferably *Neisseria meningitidis* (meningococcal) B serotype outer membrane proteins, which are T-cell stimulators. An example of these serotype proteins has been described in Helting et al., "Serotype Determinant Proteins of *Neisseria Meningitidis*", Actapath. Microbiol. Scand. Sect. C, 89, 69–78, 1981, and Frasch et al., J. Bact., 127, 973–981 (1976).

The conjugates of the instant invention may then be any stable polysaccharide-protein conjugates, coupled through bigeneric spacers containing a thioether group and alkyl amide, which form hydrolytically-labile covalent bonds with the neutral polysaccharide and the protein. Preferred conjugates according to this invention, however, are those which may be represented by the formulae, Ps-A-E-S-B-Pro or Ps-A'-S-E'-B'-Pro, wherein Ps represents a nonanionic polysaccharide; Pro represents an immunogenic protein; and A-E-S-B and A'-S-E'-B' constitute bigeneric spacers which contain hydrolytically-stable covalent thioether bonds, and which form covalent bonds (such as hydrolytically-labile ester or amide bonds) with the macromolecules, Pro and Ps. In the spacer, A-E-S-B, S is sulfur; E is the transformation product of a thiophilic group which has been reacted with a thiol group, and is represented by

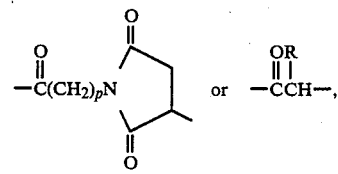

wherein R is H or CH$_3$, and p is 1 to 3; A is

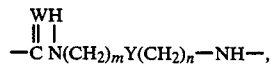

wherein
W is O or NH, m is 0 to 4, n is 0 to 3 and Y is CH$_2$, O, S, NR', or CHCO$_2$H, where R' is H or C$_1$- or C$_2$-alkyl, such that if Y is CH$_2$, then both m and n cannot equal zero, and if Y is O or S, then m is greater than 1 and n is greater than 1; and B is

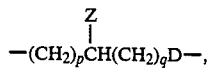

wherein q is 0 to 2, Z is NH$_2$,

COOH, or H, where R' and p are as defined above, and D is

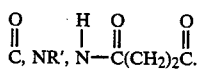

Then in the spacer, A'-S-E'-B', S is sulfur; A' is

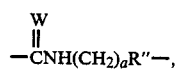

wherein a is 1 to 4 and R' is CH$_2$, or

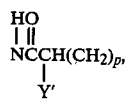

where Y' is NH$_2$ or NHCOR', and W, p and R' are as defined above, and E' is the transformation product of a thiophilic group which has been reacted with a thiol group, and is represented by

wherein R is as defined above, and B' is

or E' is

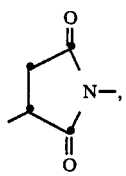

and B' is

wherein p is 1 to 3. Further, of the bigeneric spacers, A-E-S-B and A'-S-E'-B', the E-S-B and A'-S-E' components are determinable and quantifiable, with this identification reflecting the covalency of the conjugate bond linking the side of the thioethersulfur which originates from the covalently-modified nonanionic polysaccharide with the side of the spacer which originates from the functionalized protein.

In the process of the instant invention, the polysaccharide is covalently-modified by (a) fragmenting it by heating the polysaccharide in water with or without aqueous hydrazine, with the water being removed by lyophilization and drying with P$_2$O$_5$ in a vacuum, then (b) activating it with a bifunctional reagent in a non-aqueous, polar, aprotic solvent, (c) reacting this activated polysaccharide with a bis-nucleophile, and finally, if necessary, further (d) functionalizing this modified polysaccharide by either reaction, (i) with a reagent generating electrophilic (e.g., thiolphilic) sites or, (ii) with a reagent generating thiol groups. The protein is conversely either reacted (i) with a reagent generating thiol groups or (ii) with a reagent generating thiolphilic sites, then the covalently-modified polysaccharide and the functionalized protein are reacted together to form the stable covalently-bonded conjugate and the final mixture is purified to remove unreacted polysaccharides and proteins.

The process of this invention also includes selection of a nucleophile or bis-nucleophile which will react with the activated polysaccharide to form a covalently-modified polysaccharide with pendant electrophilic sites or pendant thiol groups, thereby obviating the need to further functionalize the bis-nucleophile-modified polysaccharide prior to reacting the covalently-modified polysaccharide with the covalenlly-modified protein. Also, the functionalization of the protein to either moiety form may be accomplished in more than one step according to the selection of reactants in these steps.

A. PREPARATION OF THE POLYSACCHARIDE

In the first step toward covalently-modifying the polysaccharide, the solid, largely insoluble polysaccharide must be solubilized.

Since the neutral polysaccharides of this invention are insoluble in organic solvents or salt solutions and only marginally-soluble in water, and since nucleophilic alcoholic hydroxyl groups of a polysaccharide cannnot compete chemically for electrophilic reagents with the hydroxyls of water in an aqueous solution, the polysaccharide must be modified into a more soluble form, then it should be dissolved in non-aqueous (non-hydroxylic) solvents. Suitable solvents include dimethylformamide, dimethylsulfoxide, dimethylacetamide, formamide, N,N'-dimethylimidazolidinone, and other similar polar, aprotic solvents, preferably dimethylformamide.

In U.S. Ser. No. 608,738, filed May 10, 1984, now abandoned bacterial polysaccharides with acid groups were solubilized in non-hydroxylic organic solvents by first converting them into an appropriate salt form. By contrast, Applicants accomplish the solubilization of an intact, otherwise largely insoluble neutral polysaccharide by heating these non-polyanionic, neutral polysaccharides for from 30 seconds to 10 minutes at 70° to 100° C. in distilled water which may or may not contain 5-15% aqueous hydrazine, thereby fragmenting the polysaccharides, but preserving the viability of the neutral polysaccharides for immunogenic vaccine use, but putting the polysaccharide in a usable form.

Subsequent steps are then directed to overcoming the other significant physico-chemical limitation to making covalent bonds to polysaccharides, that being the lack of functional groups on the polysaccharides, other than hydroxyl groups, which are reactive enough with reagent commonly or practically used for functionalization of units with which bonding is desired. The residual water (and hydroxyl groups) is removed by lyophilization and drying with P₂O₅ in a vacuum. Then, activation of the polysaccharide to form an activated polysaccharide, reaction with bis-nucleophiles to form a nucleophile-functionalized polysaccharide, and functionalization with reagents generating either electrophilic sites or thiol groups, are all directed to covalently-modifying the polysaccharide and developing functional groups on the polysaccharide in preparation for conjugation.

In the next step, the depolymerized polysaccharide is activated by reaction with a bifunctional reagent at about 0°–50° C., while stirring for ten minutes to one hour, with the crucial weight ratio of activating agent to polysaccharide in the range of 1:5 to 1:12. Activation with cyanogen bromide is possible according to the present invention, this reagent is poorly utilized in activation of polysaccharides and is not preferred. Instead, preferred bifunctional reagents for activating the polysaccharide include carbonic acid derivatives,

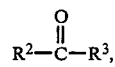

wherein R² and R³ may be independently, azolyl, such as imidazolyl; halides; or phenyl esters, such as p-nitrophenyl, or polyhalophenyl.

Carbonyldiimidazole, a particularly preferred reagent, will react with the hydroxyl groups to form imidazolylurethanes of the polysaccharide, and arylchloroformates, including, for example, nitrophenylchloroformate, will produce mixed carbonates of the polysaccharide. In each case, the resulting activated polysaccharide is very susceptible to nucleophilic reagents, such as amines, and is thereby transformed into the respective urethanes.

In the next stage, the activated polysaccharide is reacted with a nucleophilic reagent, such as an amine, particularly diamines, for example,

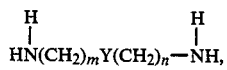

wherein m is 0 to 4, n is 0 to 3, and Y is CH₂, O, S, NR′, CHCO₂H, where R′ is H or a C₁- or C₂-alkyl, such that if Y is CH₂, then both m and n cannot equal zero, and if Y is O or S, then m is greater than 1 and n is greater than 1, in a gross excess of amine (i.e., for example, a 50- to 100-fold molar excess of amine vs. activating agent used). The reaction is kept in an ice bath for from 15 minutes to one hour then kept for 15 minutes to one hour at about 17°–40° C.

An activated polysaccharide, when reacted with a diamine, e.g., 1,4-butanediamine, would result in a urethane-form polysaccharide with pendant amines, which may then be further functionalized by acylating. Mixed carbonates will also readily react with diamines to result in pendant amine groups.

Alternatively, the activated polysaccharide may be reacted with a nucleophile, such as a monohaloacetamide of a diaminoalkane, for example, 4-bromoacetamidobutylamine (see, W. B. Lawson et al., *Hoppe Seyler's Z. Physiol Chem.*, 349 251 (1968)), to generate a covalently-modified polysaccharide with pendant electrophilic sites. Or, the activated polysaccharide may be reacted with an aminothiol, such as cysteamine (aminoethanethiol) or cysteine, examples of derivatives which are well-known in the art of peptide synthesis, to produce a polysaccharide with pendant thiol groups. In both cases, no additional functionalization is necessary prior to coupling the covalently-modified polysaccharide to the modified bacterial "carrier" protein.

The last step in preparing the polysaccharide, the further functionalization, if necessary, of the polysaccharide, may take the form of either reacting the nucleophile-functionalized polysaccharide with a reagent to generate electrophilic (i.e., thiophilic) sites, or with a reagent to generate thiol groups.

Reagents suitable for use in generating electophilic sites, include for example, those for acylating to α-haloacetyl or α-halopropionyl, derivative such as

(wherein R is H or CH₃; X is Cl, Br or I; and X′ is nitrophenoxy, dinitrophenoxy, pentachlorophenoxy, pentafluorophenoxy, halide, O-(N-hydroxysuccinimidyl) or azido), particularly chloroacetic acid or α-bromopropionic acid, with the reaction being run at a pH of 8 to 11 (maintained in this range by the addition of base, if necessary) and at a temperature of about 0° to 35° C., for ten minutes to one hour. An amino-derivatized polysaccharide may be acylated with activated maleimido amino acids (see, O. Keller et al, *Helv. Chim. Acta.*, 58, 531 (1975)) to produce maleimido groups,

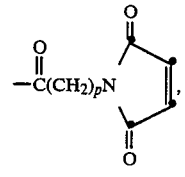

wherein p is 1 to 3; with a 2-haloacetylating agent, such as p-nitrophenylbromoacetate; or with an α-haloketone carboxylic acid derivative, e.g.,

(Ber., 67, 1204, (1934)) in order to produce appropriately-functionalized polysaccharides which are susceptible to thio substitution.

Reagents suitable for use in generating thiol groups include, for example, acylating reagents, such as thiolactones, e.g.,

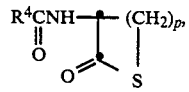

wherein R⁴ is C₁–C₄alkyl or mono- or bicyclic aryl, such C₆H₅ or C₁₀H₁₃, and p is 1 to 3;

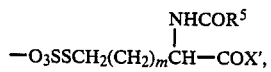

wherein m is 0 to 4, $R^5$ is $C_1$-$C_4$alkyl or $C_6H_5$, and X' is as defined above, followed by treatment with $HSCH_2CH_2OH$; or

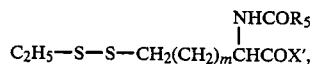

wherein m, $R^5$ and X' are as defined immediately above, then treatment with dithiothreitol. Such reactions are carried out in a nitrogen atmosphere, at about 0°–35° C. and at a pH of 8–11 (with base added, as necessary, to keep th pH within this range), for one to twenty-four hours. For example, an amino-derivatized polysaccharide may be reacted with

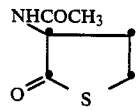

to produce an appropriately-functionalized polysaccharide.

By these steps then, covalently-modified neutral polysaccharides of the forms, Ps-A-EY-) or Ps-A'-SH-, wherein Eγ is

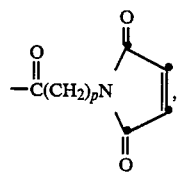

and A, A', R, X and p are as defined above, are produced.

B. PREPARATION OF THE PROTEIN

Separate functionalization of the protein to be coupled to the polysaccharide, involves reaction of the protein with one or more reagents to generate a thiol group, or reaction of the protein with one or more reagents to generate an electrophilic (i.e., thiophilic) center, as shown in U.S. Ser. No. 608,738, filed May 10, 1984.

In preparation for conjugation with an electrophilic-functionalized polysaccharide, the protein is reacted in one or two steps with one or more reagents to generate thiol groups, such as those acylating reagents used for generating thiol groups on polysaccharides, as discussed on pages 15–17 above. Thiolated proteins may also be prepared by aminating carboxy-activated proteins, such as those shown in Atassi et al., *Biochem et Biophys. Acta,* 670, 300, (1981), with aminothiols, to create the thiolated protein. A preferred embodiment of this process step involves the direct acylation of the pendant amino groups (i.e., lysyl groups) of the protein with N-acetylhomocysteine thiolactone at about 0° to 35° C. and pH 8 to 11, for from five minutes to two hours, using equiweights of reactants.

When

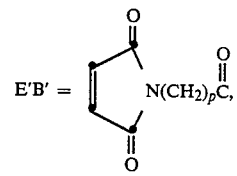

the conditions and method of preparing the functionalized protein are as discussed above on pages 15–17 for preparing the counterpart polysaccharide by reaction with activated maleimido acids.

In preparing for conjugation with a covalently-modified bacterial polysaccharide with pendant thiol groups, the protein is acylated with a reagent generating an electrophilic center, such acylating agents including, for example,

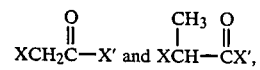

wherein X and X' are as defined above; and

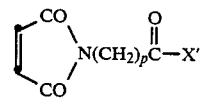

wherein X' is as defined above. Suitable proteins with electophiiic centers also include, for example, those prepared by acylation of the pendant lysyl amino groups with a reagent, such as activated maleimido acids, for example,

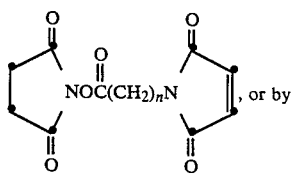

or by reacting the carboxy-activated protein with monohaloacetyl derivatives of diamines. In both preparation reactions, the temperature is from 0° to 35° C. for from five minutes to one hour and the pH is from 8 to 11.

C. FORMATION OF THE CONJUGATE

Formation of the conjugate is then merely a matter of reacting any of the covalently-modified polysaccharides having pendant electrophilic centers with any of the proteins having pendant thiol groups at a pH of 7 to 9, in approximate equiweight ratios, in a nitrogen atmosphere, for from six to twenty-four hours at from about 17° to 40° C., to give a covalent conjugate. Examples of such reactions include:

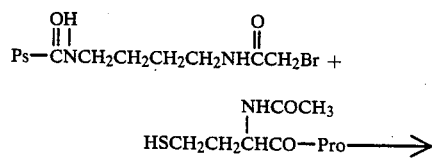

-continued

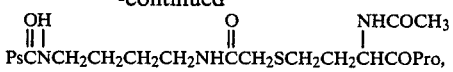

wherein an activated polysaccharide which has been reacted with 4-bromoacetamidobutylamine is reacted with a protein which has been reacted with N-acetyl-homocysteine thiolactone, to form a conjugate, and:

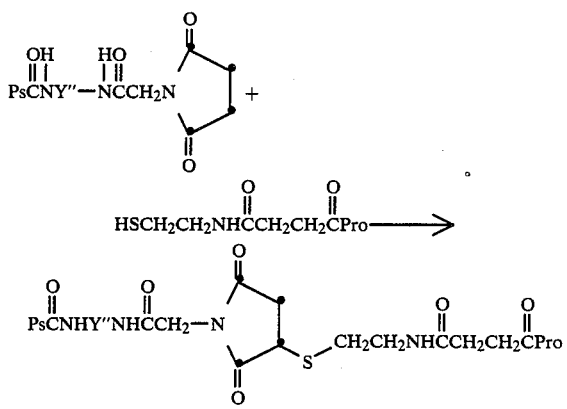

(where Y″ is a $C_2$–$C_8$alkyl radical), wherein an amino-derivatized polysaccharide which has been reacted with activated maleimido acids is reacted with a carboxy-activated protein which has been aminated with an aminothiol, to form a conjugate.

Similarly, any of the covalently-modified polysaccharides with pendant thiol groups may be reacted with any of the proteins having pendant electrophilic centers to give a covalent conjugate. An example of such a reaction is:

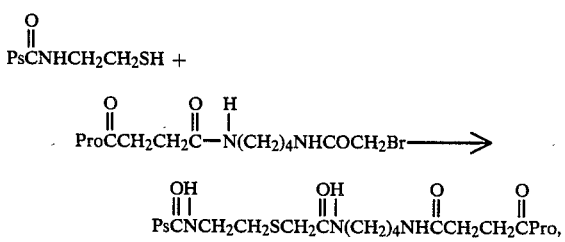

wherein an activated polysaccharide which has been reacted with an aminothiol is reacted with a carboxy-activated protein which has been reacted with monohaloacetyl derivatives of a diamine, to form a conjugate.

These conjugates are then centrifuged at about 100,000 times G using a fixed angle rotor for about two hours at about 1° to 20° C., or are submitted to any of a variety of other purification procedures, including gel permeation, ion exclusion chromatography, gradient centrifugation, or other differential adsorption chromatography, to remove non-covalently-conjugated polysaccharides and proteins, using the covalency assay for the bigeneric spacer (see below) as a method of following the desired biological activity.

D. ANALYSIS TO CONFIRM COVALENCY

Analysis of the conjugate to confirm the covalency, and hence the stability of the conjugate, is accomplished by Applicants by hydrolyzing (preferably with 6N HCl at 110° C. for 20 hours) the conjugate, then quantitatively analyzing for the amino acid of the hydrolytically-stable spacer containing the thioether bond and constituent amino acids of the protein. The contribution of the amino acids of the protein may be removed, if necessary, by comparison with the appropriate amino acid standard for the protein involved, with the remaining amino acid value reflecting the covalency of the conjugate, or the amino acid of the spacer may be designed to appear outside the amino acid standard of the protein in the analysis. The covalency assay is also useful to monitor purification procedures to mark the enhancement of concentration of the biologically-active components. In the above examples, hydrolysis of

results in the release of S-carboxymethylhomocysteine,

hydrolysis of

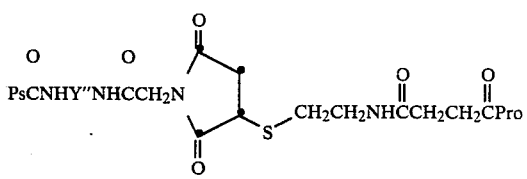

results in the release of the aminodicarboxylic acid,

and hydrolysis of

results in the release of S-carboxymethylcysteaomine. $H_2HCH_2CH_2SCH_2CO_2H$ by cleavage of the Ps-A-E-S-B-Pro molecule at peptide linkages and other hydrolytically-unstable bonds. Chromatographic methods, such as those of Spackman, Moore, and Stein, may then be conveniently applied and the ratio of amino acid constituents determined.

E. APPLICATIONS

One or more of the conjugates of this invention may be used in mammalian species for either active or passive protection, prophylactically or therapeutically, against bacteremia caused by the cognate organism. In preferred embodiments of this invention, the conjugates of this invention may be used in mono- or polyvalent vaccines, either alone; with other conjugates containing other neutral polysaccharides such as *Streptococcus pneumoniae* 7F, 14 and 37; with other conjugates containing polyanionic polysaccharides, such as *Haemophilus influenzaet* type b or *Streptococcus pneumoniae* type 6B, 19F or 23F organisms; or with unconjugated polysaccharides, such as *Streptococcus pneumoniae* type 3 polysaccharide.

Active protection may be accomplished by injecting an effective amount (a quantity capable of producing measurable amounts of antibodies, e.g., 2 to 50 µg) of polysaccharide in the conjugate form of each of the conjugates being administered per dose or of unconjugated polysaccharides being administered per dose, whole antiserum obtained from animals previously dosed with the conjugate or conjugates, or globulin or other antibody-containing fractions of said antisera, with or without a pharmaceutically-acceptable carrier, such as aseptic saline solution. Such globulin is obtained from whole antiserum by chromatography, salt or alcohol fractionation or electrophoresis. Passive protection may be accomplished by standard monoclonal antibody procedures or by immunizing suitable mammalian hosts. The use of an adjuvant (e.g., alum) is also intended to be within the scope of this invention.

In a preferred embodiment of this invention, monovalent or polyvalent compositions including, inter alia, the conjugates according to the invention, are used for active immunogenic vaccination of humans, especially neonates and infants. For additional stability, these conjugates may also be lyophilized in the presence of lactose (for example, at 50 µg/ml of pneumococcal polysaccharide/10 mg/ml lactose) prior to use.

A preferred dosage level is an amount of each of the conjugates or derivative thereof to be administered corresponding to 25 µg of polysaccharide in the conjugate form for conjugates of pneumococcal polysaccharides, 25 µg of unconjugated polysaccharides and dosages of conjugates or derivatives thereof of conjugates containing polyanionic polysaccharides according to U.S. Ser. No. 608,738, filed May 10, 1984 now abandoned, in a single administration. If necessary, an additional one or two doses of conjugate or derivative thereof of the *H. influenzae* type b polysaccharide in an amount corresponding to 10 µg of the polysaccharide in the conjugate form, may also be administered.

The invention is further defined by reference to the following examples, which are intended to be illustrative and not limiting.

EXAMPLE 1

PREPARATION OF *STREPTOCOCCUS PNEUMONIAE* TYPE 14 CAPSULAR POLYSACCHARIDE

INOCULUM AND SEED DEVELOPMENT

A Stage: Working Seed Preparation

A lyophilized tube of *Streptococcus pneumoniae* type 14 bacteria inoculum seed (received from Dr. Robert Austrian of the University of Pennsylvania) was suspended in 1 ml of sterile beef heart infusion broth (25 gm of Heart Infusion Broth (Difco) in 0.9 liters of water) and this suspension was spread on five rabbit blood agar (20 gm purified agar, 25 gm heart infusion broth, 100 ml defibrinated rabbit blood, 0.9 liter distilled water) plates with approx. 0.2 ml of culture each. After approx. 18 hours incubation at 37° C., the growth on the plates was resuspended on each rabbit blood agar plate (with 5 ml of beef heart infusion broth each) and pooled.

One-half milliliter of this resuspended growth was used to inoculate each of 6 flasks of liquid blood medium (90 ml of beef heart infusion broth and 10 ml of defibrinated rabbit blood), which were then incubated without agitation at 37° C. for approx. 18 hours.

B Stage: 2-Liter Non-baffled Erlenmeyer Flasks

Two of the flasks of *Streptococcus pneumoniae* type 14 bacteria working seed from A Stage were combined and 20 ml of this seed was inoculated into each of five 2-liter non-baffled Erlenmeyer flasks containing 900 ml of sterile pneumococcus inoculum medium (see below) and 100 ml of 25% dextrose solution. The pH of the flasks was maintained at pH 6.0–7.0 by the addition of 12% sodium bicarbonate solution and after 7 hours incubation at 37° C., (at which time a typical $OD_{660}$ value was 2.90) the growth from four of the flasks was pooled (the pool having an $OD_{660}$ of 2.80 and a pH of 6.8).

| Pneumococcus Inoculum Medium γ | |
|---|---|
| Soya Peptone | 20 gm |
| Yeast Extract Ultrafiltrate (1) | 100 ml |
| NaCl Reagent | 5 gm |
| K₂HPO₄ | 2.5 gm |
| 2% Phenol Red | .5 ml |
| Distilled Water | 1 liter |

γThe solution was sterilizdd by autoclaving at 121° C. for 25 minutes.

The salts and soya peptone were dissolved in small volumes of hot, pyrogen-free water and brought to correct final volume with additional hot, pyrogen-free water. The fermenters or flasks were then sterilized for about 25 minutes at 121° C. and after cooling, the yeast extract ultrafiltrate (1) was added aseptically to the flasks or fermenters prior to inoculation.

(1) Yeast extract ultrafiltrate: 100 g brewers' yeast extract (Amber) was dissolved in 1 liter distilled water and ultrafiltered in an Amicon DC-30 hollow fiber with H10X50 cartridges to remove molecules with m.w. 50,000. The filtrate was collected and passed through a 0.22µmembrane as a sterile product.

C Stage: 70-Liter Seed Fermenter

The pooled product of B Stage was used to inoculate a 70-liter fermenter containing the Pneumococcus Seed Medium (prepared as described below), with a starting pH of 6.8.

The fermentation was maintained at 37° C. with 100 rpm agitation and monitored by optical density (O.D.), glucose test and pH determinations until an (O.D.) of 3.25 was reached (after about 4 hours).

| Complete Pneumococcus Seed Medium | |
|---|---|
| Soya Peptone | 800 gm |
| Yeast Extract Ultrafiltrate (1) | 4 liters |
| K₂HPO₄ Reagent | 100 gm |
| NaCl Reagent | 200 gm |
| 25% Dextrose Solution (2) | 4 liters |
| Ucon B625 Antifoam | 14 ml |
| Distilled Water | 31.8 liters |

(2) Dextrose was prepared as a sterile 25% solution in glass-distilled water, and added to the 70-liter fermenter with the yeast extract ultrafiltrate.

D Stage: 800-Liter Production Fermenter

Approximately 40 liters of the product of C Stage was used to inoculate an 800-liter fermenter containing 530 liters of Pneumococcus Production Medium (prepared as described below).

The fermentation was maintained at 37° C. with 100 rpm of agitation, with the O.D., glucose and pH levels being checked about every two hours until the O.D. was similar for a two-hour period, at which time the fermentation was terminated (a typical final O.D. was 5.2 after 6 hours.).

| Pneumococcus Production Medium | |
|---|---|
| Soya Peptone | 10.5 kg |
| Yeast Extract Ultrafiltrate (1) | 52.5 liters |
| K$_2$HPO$_4$ Reagent | 1.313 kg |
| NaCl Reagent | 2.625 kg |
| 25% Dextrose Solution (2) | 58 liters |
| Ucon B625 Antifoam | 95 ml |
| Distilled Water | 418.5 liters |

HARVEST AND INACTIVATION

The batch was inactivated by harvesting into a "kill tank" containing 8.2 liters of liquified phenol.

34 and 58% ETHANOL PRECIPITATION

To 640 liters of the killed culture, 213.3 liters of 95% ethanol was added, at 3.6 liters/minute with stirring at 20 to 26° C., then 117 liters of 95% ethanol was added, at 2 liters/minute, to a total final volume of 950 liters and a final concentration of 35% ethanol by volume. The mixture was stirred four additional hours at 22° C. to ensure complete fractionation, and the supernatant fluid was collected through a bank of five 4-inch Sharples centrifuges at 15,000 rpm (flow rate of approx. 4 liters/min). The insoluble pellet was discarded and the clarified fluid was brought to 58% ethanol with the addition of 559 liters of additional 95% ethanol at 7.6 liters/minute. The mixture was stirred at 21° C. for five additional hours to insure complete precipitation.

RECOVERY OF THE SECOND PELLET

The resulting 34% ethanol soluble-58% ethanol-insoluble precipitate was collected by centrifugation in the 4-inch Sharples centrifuge at 15,000 rpm (flow rate of approx. 4 liters/min.) and the 58% ethanol supernatant fluid was discarded. The crude product yield was 2.435 kg of wet paste.

24% ISOPROPYL ALCOHOL PRECIPITATION

The 2.435 kg of 58% ethanol-insoluble material was combined with 1.626 kg of material produced from a second fermentation in a like manner and the resulting 4.061 kg of material was mixed in a Daymax dispersion vessel at 15° to 29° C. with 30 liters of glass-distilled water for 12 minutes until the suspension was homogeneous. Approximately 66 additional liters of distilled water were added to the suspension and this mixture was agitated for four hours. Twenty-four liters of 5% sodium acetate solution was added to the mixture and the pH was adjusted to 6.5 by the addition of glacial acetic acid.

The 120 liters of solution was brought to 24% isopropyl alcohol concentration by the addition of 37.9 liters of isopropanol at 0.3 liters/minute under agitation at 15° to 29° C. After additional stirring for 4 hours, the mixture was centrifuged through a 4-inch Sharples centrifuge at 15,000 rpm (flow rate=0.35 liters/minute) for 5.75 hours, and through an Electronucleonics K3- Ultracentrifuge (28,000 rpm) at 200–400 ml/min until the effluent appears clear, and the insoluble pellet was discarded.

39% ISOPROPYL ALCOHOL PRECIPITATION AND COLLECTION OF CRUDE PRODUCT PASTE

The 24% isopropyl-soluble supernatant fluid from the previous step was brought to 39% isopropanol by the addition of 38.8 liters of isopropyl alcohol, at 0.3 liters/minute with stirring. The mixture (194 liters) was then allowed to stand with agitation for 3.25 hours, then was centrifuged for about 18 hours in two 4-inch Sharples units at 15,000 rpm (flow rate=0.5 liters/minute) to collect the pelleted crude polysaccharide (2.006 kg).

DIAFILTRATION

The pellet from the centrifugation was transferred to the Daymax mixer containing 20 liters of distilled water and mixed for 30 minutes until the suspension was homogeneous. This suspension was then diluted with 300 liters of cold, glass-distilled water and diafiltered to a constant conductance at about 23° C. on an Romicon ultrafiltration apparatus using ten HF26.5-45-XM50 cartridges. The retentate was concentrated to a minimum volume, the Romicon unit was rinsed and the rinse added to the retentate, such that the final volume was 86 liters. The ultrafiltrate was discarded.

CETAVLON PRECIPITATION 1.84 Kg of Cetavlon (N,N,N-trimethyl-1-hexadecanaminium bromide) was dissoved in 6 liters of distilled water and this solution was added, with agitation, over approximately 1 hour, to the 86 liters of retentate from the previous step. After aging for 4 hours, the precipitated impurities (1.925 kg) were collected by centrifugation in the K3 Ultracentrifuge (28,000 rpm), at 5° C. for 8 hours, and the supernatent fluid collected.

ISOPROPANOL FRACTIONATION 28.55 Kg of sodium acetate trihydrate was added over 10 minutes to the 86 liters of the supernatant from above, with agitation, and the pH of the solution was adjusted to 6.6 with glacial acetic acid. The solution was brought to 28% isopropanol with 45.1 liters of isopropanol at 0.38 liters/minute with agitation, and, after 4 additional hours of agitation, fed into the K3 Ultracentrifuge (28,000 rpm), from which 12 grams of precipitate was collected, and discarded. 38.9 Liters of isopropanol (final conc.=42%) was added at 0.3 liters/minute to the 116 liters of supernatant, with agitation, and, after 4 additional hours of agitation, the solution was circulated to two 4-inch Sharples centrifuges, at 15° to 29° C., at 15,000 rpm (1.3 liter/minute flow rate each), and the effluent was discarded.

TRITURATION AND COLLECTION OF FINAL PRODUCT

The resulting polysaccharide pellet was triturated in a 1-gallon Waring blender using the 30 seconds on-30 seconds off method with 3 liters of absolute ethanol, until the paste became a hard white powder. This powder was collected on a Buchner funnel fitted with a teflon filter disc, and washed in situ with four 1-liter portions of absolute ethanol and with two 2-liter portions of acetone. The product was removed from the funnel and transferred to tared dishes for drying in vacuo at 20° to 25° C. (for about 18 hours). The final yield of the product was 315.2 grams dry weight, add its properties were as follows:

TABLE 1-1
PNEUMOCOCCAL TYPE 14 POLYSACCHARIDE CHEMICAL ASSAY DATA

| Assay | Result |
| --- | --- |
| Moisture (TG) | 6.3% |
| Protein | 4.8% |
| Nucleic Acid | 0.6% |
| Hexosamine | 28.6% |
| Nitrogen | 1.6% |
| Phosphorus | 0.2% |
| Molecular sizing (KD on Sepharose 4B) | 0.19–0.21 |

The following procedures were used in performing the above assays.
1. Moisture—Standard thermogravimetry (wt. loss to 100° C.) using a Perkin-Elmer thermobalance TSG-1.
2. Protein—Lowry method; Lowry et al., J. Biol. Chem., 193: 265 (1951).
3. Nucleic Acid—U. V. method; Warburg and Christian, Biochem Z., 310: 384 (1942).
4. Hexosamine—Elson and Morgan, Biochem. J., 27: 1824 (1933).
5. Nitrogen—Combustion method using Perkin-Elmer 240-CHN elemental analyzer.
6. Phosphorus—Molybdate method; Chen et al., Anal. Chem. 28: 1756 (1956).

EXAMPLE 2

PREPARATION OF NEISSERIA -MENINGITIDIS Bll SEROTYPE 2 MEMBRANE PROTEIN

A. Fermentation

1. *Neisseria meningitidis* Group B11

A tube containing the lyophilized culture of *Neisseria meningitidis* (obtained from Dr. M. Artenstein, Walter Reed Army Institute of Research (WRAIR), Washington, D.C.) was opened and Eugonbroth (BBL) was added. The culture was streaked onto Chocolate agar plates (BBL) and incubated at 37° C. with 5% $CO_2$ for 36 hours, at which time the growth was harvested into 10% skim milk medium (Difco), aliquoted and frozen at −70° C. The organism was positively identified by agglutination with specific antiserum supplied by WRAIR and typing serum supplied by Difco.

This first-passage culture was streaked onto Chocolate agar plates and incubated at 37° C. with 5% $CO_2$ for 18 hours, at which time the growth was harvested into 10% skim milk medium, aliquoted into 1 ml amounts and frozen at −70° C. The organism was again positively identified by agglutination with specific antiserum supplied by WRAIR and typing serum supplied by Difco.

A vial of the culture from the second passage was thawed and streaked onto 10 Columbia Sheep Blood agar plates (CBAB-BBL). The plates were incubated at 37° C. with 5% $CO_2$ for 18 hours, after which time the growth was harvested into 100 ml of 10% skim milk medium, aliquoted in 0.5 ml amounts and frozen at −70° C. The organism was positively identified by agglutination with specific antiserum, sugar fermentation and gram stain.

A vial of the culture from this this passage was thawed, diluted with Mueller-Hinton Broth and streaked onto 40 Mueller-Hinton agar plates. The plates were incubated at 37° C. with 6% $CO_2$ for 18 hours after which time the growth was harvested into 17 ml of 10% skimmed milk medium, aliquoted in 0.3 ml amounts and frozen at −70° C. The organism was positively identified by Gram stain, agglutination with specific antiserum and the oxidase test.

2. Fermentation and collection of cell paste a. Inoculum Development

The inoculum was grown from two 0.5 ml frozen vials of *Neisseria meningitidis* Group B, B-11 from above (passage 4). Four Mueller-Hinton agar Blake bottles were inoculated, harvested approximately 18 hours later, and used as an inoculum for 5 liters of Gotschlich's yeast dialysate medium at pH 7.29. The O.D. was adjusted to 0.065 at 660 nm (Perkin Elmer). The organism was grown in 5 two-liter Erlenmeyer flasks (each containing 1 liter of medium; see below) at 37° C. in a shaker. The O.D. was monitored at 45−, 75−and 120−minute intervals. Approximately 4 liters of broth culture, at an $O.D._{660}$ of 0.81 (Spectronic 20), resulted.

A 3 ml sample was taken for Gram stain, isolation streakes onto CBAB, Mueller, Hinton, and yeast extract dextrose plates and agglutination check. All reactions were satisfactory.

70 Liter Seed Fermenter

Approximately 3600 ml of seed culture was used to inoculate a sterile 70-liter fermenter containing 42.6 liters of complete production medium (see below).

The conditions for the 70-liter fermentation included 37° C., 185 rpm with 10 liters/minute air sparging and constant pH control at pH 7.0 for 5.5 hours.

The culture was plated onto Mueller-Hinton agar plates, yeast extract dextrose and rabbit blood agar plates (Merck) at 37° C. and tested for agglutination with *N. meningitidis* group B antiserum. The growth on Mueller-Hinton agar plates, yeast extract dextrose plates and rabbit blood agar plates was normal and the agglutination reaction was positive. For this batch, the final O.D. was 0.840 at 660 microns after 5.5 hours.

c. 800-Liter Production Fermenter

Approximately 46.2 liters of seed culture were used to inoculate a sterile 800 liter fermenter containing 568.2 liters of complete production medium (see below). The batch was incubated at 37° C., 100 rpm with 60 liters/-minute air sparging and constant pH control at pH 7.0.

Before the batch was inactivated, the culture was plated on Mueller-Hinton agar plates, yeast extract dextrose plates and rabbit blood agar plates at 37° C. and tested for agglutination with *N. meningitidis* group B antiserum. The growth on Mueller-Hinton agar plates, yeast extract dextrose and rabbit blood agar plates was normal and the agglutination reaction was positive. For this batch, the final O.D. was 2.24 thirteen hours after inoculation.

| 3. Complete Medium for nephelometer flasks and 70- and 800-liter fermenters | |
|---|---|
| Fraction A | |
| L-glutamic acid | 1.5 g/liter |
| NaCl | 6.0 g/liter |
| $Na_2HPO_4$.anhydrous | 2.5 g/liter |
| $NH_4Cl$ | 1.25 g/liter |
| KCl | 0.09 g/liter |
| L-cysteine HCl | 0.02 g/liter |

Fraction B (Gotschlich's yeast dialysate)

1280 gm of Difco Yeast Extract were dissolved in 6.4 liters of distilled water. The solution was dialyzed in 2 Amicon DC-30 hollow fiber dialysis units with three H10SM cartridges. The dialysate and 384 gm $MgSO_4 \cdot 7-H_2O$ and 3200 gm dextrose were dissolved in the dialysate and the total volume brought up to 15 liters with distilled water. The pH was adjusted to 7.4 with NaOH and sterilized by filtration through Millipore (0.22μ) and added to the fermenter containing Fraction A.

For the Nephleometer flasks: 1 liter of Fraction A and 25 ml of Fraction B were added and the pH was adjusted to 7.0-7.2 with NaOH.

For the 70-liter fermenter: 41.8 liters of Fraction A and 900 ml of Fraction B were added and the pH was adjusted to 7.0-7.2 with NaOH.

For the 800-liter fermenter: 553 liters of Fraction A and 15.0 liters of Fraction B were added and the pH was adjusted to 7.0-7.2 with NaOH.

d. Harvest and Inactivation

After the fermentation was completed, phenol (0.5% v/v final concentration) was added to a separate vessel, to which the cell broth was then transferred. The material was held at room temperature with gentle stirring until the culture was no longer viable (about 24 hours).

e. Centrifugation

After about 24 hours at 4° C., the 614.4 liters of inactivated culture fluid was centrifuged through Sharples centrifuges. The weight of the cell paste after phenol addition was 3.875 kg.

B. Isolation

Step 1. Washing of Bacterial Cells

For each isolation, a two hundred gram aliquot of the above 0.5% phenol-inactivated paste was suspended in a 800 ml portion of sterile distilled water and stirred magnetically to granular suspensions. The suspended cells were peleted at 20,000 xg for 60 minutes at 5° C. (Beckman 19 Ti rotor, 14,500 rpm).

Step 2. Extraction

The washed cells were suspended in 2000 ml of 0.1M Tris-0.01M EDTA Buffer pH 85 with 0.5% sodium deoxycholate (TED Buffer) with a Sorvall 2 quart omnimixer at setting 3 for 60 seconds. The homogeneous suspension was tranferred to 16 Erlenmeyer 500 ml flasks for extraction at 56° C. in a shaking waterbath for 15 minutes (at temperature).

The extract was centrifuged at 20,000 xg for 60 minutes at 5° C. (Beckman 19 Ti rotor, 14,500 rpm). The viscous supernatant fluids were then decanted (total volume=1980 ml) and stored at 4° C.

The extracted cell pellets were resuspended in 2000 ml TED Buffer as described immediately above. The suspension was extracted for 15 minutes at 56° C. and centrifuged as above. The supernatant fluids were decanted (volume=2100 ml) and stored at 4° C.

Step 3. Concentration by Ultrafiltration

The extraction supernatants from Step 2 were pooled (total volume=4005 ml). Two liters of the pool were dispensed into a 2 liter New Brunswick fermentation vessel attached to a Millipore Pellicon filter apparatus fitted with two 0.45 micron durapore membranes (½ sq. ft. surface area). The extract supernatant was held at 25° C. in the fermentation vessel throughout the 90-minute concentration process. The sample was concentrated tenfold at an average transmembrane pressure of 27.5 psi.

Step 4. Collection and Washing of the Serotype Protein

The retentate from Step 3 (205 ml) was centrifuged to pellet the serotype protein at 160,000 xg for 2 hours at 5° C. (Beckman 45 Ti rotor, 37,000 rpm). The supernatants were decanted and discarded.

The protein pellets were weighed (8.12 grams) and then suspended in TED Buffer (190 ml buffer; 20 ml/gram pellet) manually with a glass rod and a Dounce homogenizer. The suspension was extracted at 56° C. for 15 minutes (at temperature) in a 500 ml Erlenmeyer flask with shaking. The suspension was centrifuged at 160,000 xg for 2 hours at 5° C. (Beckman 45 Ti rotor, 37,000 rpm). The supernatant fluid was decanted and discarded (volume=190 ml). The pellets were washed a second time in 190 ml of TED Buffer, as above.

Step 5. Recovery of Product

The washed protein pellets from Step 4 were suspended in 100 ml distilled water with a glass rod and a Dounce homogenizer to insure complete suspension. A Lowry Protein value of 17.0 mg/ml was obtained for this suspension. At this point. 200 mg of the suspension were reserved for experimental use. The remaining bulk suspension 91 ml) was diluted to 8.0 mg/ml with 102.4 ml glass distilled water. The aqueous suspension was centrifuged at 12,000 xg for 15 minutes to clear it of aggregates (Beckman 45 Ti rotor, 10,000 rpm).

The supernatant product was withdrawn carefully by pipet to avoid the soft aggregate pellet. The product was labeled (volume=182.5 ml) and aliquots were assayed for sterility and pyrogen (sterile product; no pyrogens). The product was stored at 4° C. as as sterile bulk until use in conjugation at which time it was analytically characterized. The Yield was 9.5 mg Lowry Protein/gram of original cell paste.

TABLE 2-1

| MENINGOCOCCAL B SEROTYPE 2 PROTEIN SOLUTION CHEMICAL ASSAY DATA | |
|---|---|
| Assay | Result |
| Protein Lowry | 4.1 mg/ml |
| Nucleic Acid* | |
| RNA (Bial) | 1.8% |
| DNA (Diphenylamine) | 0.6% |
| Neutral Sugars* Anthrone | 1.05 |
| Sialic Acid* | 3.0% |
| Molecular Weight SDS-PAGE | 40,000d |

*Calculated as percent of Lowry protein.

The following procedures were used in performing the assays:

1. Protenin—as in Example 1.

2. Nucleic Acid—Color development was observed with the orcinol reaction (Bial) which corresponded to 1.8% RNA calculated as a percentage of the protein concentration. The diphenylamine test for DNA indicated a 0.6% DNA content calculated as a percentage of the protein in the bulk solution.

3. Neutral Sugars—The neutral sugar content calculated as a percentage of protein was found using the anthrone colorimetric test. (Scott and Melvin, Anal. Chem. 25, 1656, 1953).

4. Sialic Acid—The sialic acid content was found using the resorcinol-HCl method (Svennerholm, Biochem. Biophys., Acta 24, 604, 1957).

Molecular Weight—The molecular weight of the mercaptoethanol denatured protein as determined by SDS polyacrylamide gel electrophoresis (Nature 227:680 (1970), LKB Application Note 306).

EXAMPLE 3

PREPARATION OF S. PNEMONIAE TYPE 14 POLYSACCHARIDE—N. MENINGITIDIS B SEROTYPE OUTER MEMBRANE PROTEIN CONJUGATE USING CENTRIFUGATION IN THE CONJUGATION STEP

I. Fragmentation of pneumococcal type 14 polysaccharide with aqueous hydrazine A 100 ml round bottom flask was charged with 24 ml of $H_2O$ and 1.92 ml of 97% hydrazine and then treated in a boiling water bath until the temperature was 100° C. (about 3 minutes). To this was added, in one portion, 240 mg of S. Pneumoniae type 14 polysaccharide (Pn 14) and the resultant solution was rapidly stirred for 1.0 minute. The flask was then cooled rapidly in an ice bath and its contents were dialyzed in Spectropor 2 tubing (m.w. cutoff 12,000–14,000) vs. 32 L of $H_2O$ for 5 hours. Then dialysis was repeated in a fresh 32 L of $H_2O$ for 16 hours. The dialysate was transferred to a 50 ml centrifuge tube and centrifuged in a clinical centrifuge to remove a sludge. The supernatant was lyophilized affording 163 mg of fragmented Pn 14.

II. Formation of the butanediamine derivative of depolymerized Pn 14

150 mg of fragmented Pn 14 were charged to a dry 50 ml round bottom flask and covered with 9 ml of dimethyl sulfoxide (DMSO) and sealed under $N_2$. The mixture was stirred for 5.0 minutes at 54° C. and then 5 minutes at room temperature. Almost all of the fragmented Pn 14 was in solution at this point. 36 mg of carbonyl diimidazole were then added and the solution stirred for 40 minutes. During this time a 1,4-butanediamine dihydrochloride solution (300 mg/6 ml of $H_2O$; pH adjusted to 9.45 with 2.5N NaOH) was prepared and cooled in an ice bath. After the 40 minutes stirring the DMSO solution was added to the cooled butane diamine solution and stirred at room temperature for 4.5 hours. It was then dialyzed vs 30 L of $H_2O$ for 17.25 hours and then a fresh 4 L of $H_2O$ for four hours. The resultant dialysate was freeze-dried affording 152 mg of the butane diamine derivative of Pn 14, Pn-BuA$_2$. $K_D=0.70$ rate naphelometry units (153% of base polysaccharide); Fluorescamine titer=150 nm NH$_2$/mg.

III. Bromoacetylation of the 1,4-butanediamine derivative of Pn 14 (Pn 14-BuA$_2$)

140 mg of Pn-14-BuA2 were dissolved in 10 ml of a pH 9.15 buffer and to this solution was added 140 mg p-nitrophenyl bromoacetate dissolved in 1 ml of acetonitrile. This was stoppered and stirred at 4° C. for 22.5 hours. It was then dialyzed vs 4 L of $H_2O$ for 6 hours, a fresh 4 L of $H_2O$ for 16 hours and a third 4 L of $H_2O$ for 7 hours. The dialysate was then lyophilized affording 139 mg of the bromoacetyl derivative of Pn 14-BuA$_2$ (Pn 14-BuA$_2$-BrAc). $K_D=0.79$ Rate nephelometry units=120% of base polysaccharide Fluorescamine titer=6 nanomoles/mg by difference ($\Delta=150$-6) it indicates 144 nanomoles of bromoacetyl groups/mg.

IV. Conjugation of Pn 14-BuA$_2$-BrAc to Functionalized N Meningitidis Protein (NMP)

All centrifugations were performed in polycarbonate tubes and unless otherwise noted at 43,000 r.p.m. for 2 hours at 4° C. in a Beckman Ti 75 rotor.

The unfunctionalized protein (10 ml, 5.5 mg/ml) was centrifuged and the pellet was resuspended using a Dounce homogenizer in 7 ml of a thiolation mixture containing of 59 mg of ethylenediamine tetraacetic acid, 11.2 mg of dithiothreitol and pH 11.3 sodium borate buffer. After it is resuspended the mixture is transferred to a centrifuge tube, capped with a serum stopper and the air replaced with $N_2$. This was transferred to a nitrogen box and to it was added 54 mg of N-acetylhomocysteine thiolactone. It was stoppered and then aged, in the $N_2$ box for 22 hours and then its pH was adjusted to 8.0 by addition of 1M KH$_2$PO$_4$. The resultant mixture was centrifuged and the pellet then resuspended in 10 ml of 0.1 M PO$_4$ pH 8.0 buffer. This was then recentrifuged to remove the remaining small molecules. The second pellet was resuspended, using a Dounce homogenizer, in 8.5 ml of pH 8.0 buffer. The Ellman assay indicates a total of 6.4 $\mu$moles of thiol.

To the resuspended thiolated protein was added 50 mg of Pn 14-BuA$_2$BrAc add the resulting solution aged for 17 hours at room temperature in the nitrogen box. It was then dialyzed vs. 4 L of $H_2O$ for 6 hours. One half of the solution (5 ml) was transferred to a centrifuge tube and 4.0 g CsCl dissolved in it. The tube was filled to the top (10 ml) with $H_2O$ and centrifuged for 20 hours at 43,000 r.p.m. at 4° C. in a Ti 75 rotor. The resultant CsCl gradient density centrifugate was fractionated, using a Haake Buchler auto Densi Flow 2C apparatus, in 1.3 ml fractions. Nine fractions were collected and numbers 5,6,7 were combined, charged to a centrifuge tube, 3.5 g of CsCl was added, the mixture was topped with $H_2O$ and centrifuged for 24 hours as above. The centrifugate was fractionated as above, the appropriate fractions detected by rate nephelometry and fractions 3 and 4 were dialyzed vs. 4L of 0.1M P$_4$ buffer (pH 7) for 16 hours and then vs. 4L of $H_2O$ for 4 hours. The resultant dialysate was diluted to 10 ml with $H_2O$.

| Found: | polysaccharide | 0.205 mg/ml |
| | protein | 0.550 mg/ml |
| Spinco: | S—carboxymethylhomocysteine: | .020 $\mu$moles |
| | lysine | .156 $\mu$moles |
| | ratio | 0.128 |

EXAMPLE 4

PREPARATION OF S. PNEUMONIAE TYPE 14 POLYSACCHARIDE N MENINGITIDIS B SEROTYPE OUTER MEMBRANE PROTEIN CONJUGATE USING A COLUMN IN THE CONJUGATION STEP

The bromoacetylated 1,4-butanediamine derivative of pneumococcal type 14 polysaccharide, prepared according to Steps I, II and III of Example 3 was then conjugated to the protein prepared according to Example 2 in a variation of Step IV of Example 3.

Conjugation of Pn 14-BuA₂-BrAc to the Outer
Membrane Protein of *Neisseria Meningitidis* (NMP)

1.2 ml of a solution of NM 1, antisera derived from said conjugates, or gamma-globulin or other antibody-containing fractions of said antisera, and a pharmaceutically-acceptable carrier.

7. A composition according to claim 6, further comprising an adjuvant.

8. A composition according to claim 6, wherein the polysaccharide-protein conjugates comprise a pneumococcal type 14 polysaccharide coupled through a bigeneric spacer of the formula,

to a meningococcal B serotype outer membrane protein, an immunologically-effective amount is an amount of each of the conjugates in the composition such that each conjugate contains from 2–50 µg of the polysaccharide in the conjugate form, and the mammalian species is humans.

9. A method of treating mmmalian species against the bacteremia of the cognate organisms, which comprises administering to said species an immunolgocially-effective amount of a composition comprising one or more types of polysaccharide-protein conjugates comprising neutral bacterial capsular polysaccharides coupled, through bigeneric spacers containing thioether onds and represented by the formula A-E-S-B, wherein E is

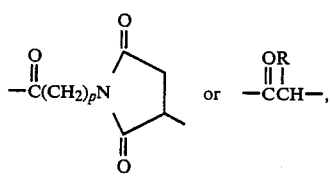

wherein R is H or $CH_3$; A is

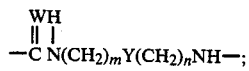

where m is 0 ,to 4, n is 0 to 3, W is 0 or NH, and Y is $CH_2$, O, S, NR', or $CHCO_2H$, where R' is H or $C_1$- or $C_2$-alkyl, such that when Y is $CH_2$, then both m and n are not equal to zero, and when Y is O or S, then m is O or S, then m is 2, 3 or 4 and n is 2 or 3; and B is

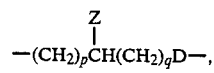

where p is 1–3, q is 0–2, Z is $NH_2$,

$CO_2H$ or H, and D is

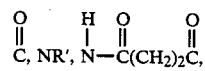

where R' is as defined above, to immunogenic proteins, and a member of the group consisting of a pharmaceutically-acceptable carrier, an adjuvant, and a pharmaceutically-acceptable carrier and adjuvant.

10. A method of treating mannalian species according to claim 9, wherein said polysaccharide-protein conjugates comprise a pneumococcal type 14 polysaccharide coupled through a bigeneric spacer of the formula

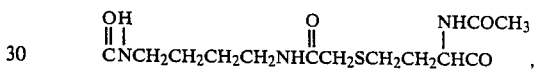

to a meningococcal B serotype outer membrane protein, the species to be treated is human neonates, and the effective amount of the composition in a single dose is an amount corresponding to 25 µg of the polysaccharide in the conjugate form for confugates of pneumococcal polysaccharides.

11. A method of treating mammalian species according to claim 9, wherein one or two additional booster compositions of an amount of a polysaccharide-protein conjugate comprising neutral bacterial capsular polysaccharides coupled through bigeneric spacers to immunogenic proteins corresponding to 25 µg of polysaccharide in the conjugate form may be administered to human neonates.

* * * * *

UNITED STATES PATENT AND TRADEMARK OFFICE
CERTIFICATE OF CORRECTION

PATENT NO. : 4,830,852

DATED : May 16, 1989

INVENTOR(S) : Stephen Marburg, Richard L. Tolman and Deborah A. Jorn.

It is certified that error appears in the above-identified patent and that said Letters Patent is hereby corrected as shown below:

Column 24, line 17, change "$CH_2O$" to --$CH_2$,O--.

Column 24, line 30, change "$CP_2H$" to --$CO_2H$--.

Column 24, line 30, change "h" to --H--.

Column 25, line 21, change "mmmalian" to --mammalian--.

Column 25, line 27, change "onds" to --bonds--.

Column 25, line 44, change "O or NH" to --O or NH--.

Column 26, line 2, delete "O or S, then m is".

Column 26, line 23, change "mannalian" to --mammalian--.

Column 26, line 36, change "confugates" to --conjugates--.

Signed and Sealed this

Twenty-sixth Day of November, 1991

Attest:

HARRY F. MANBECK, JR.

*Attesting Officer*     *Commissioner of Patents and Trademarks*